United States Patent
Zhu et al.

(10) Patent No.: US 12,269,885 B2
(45) Date of Patent: Apr. 8, 2025

(54) ANTI-PD-L1/VEGF BIFUNCTIONAL ANTIBODY AND USE THEREOF

(71) Applicant: HUABO BIOPHARM (SHANGHAI) CO., LTD., Shanghai (CN)

(72) Inventors: Xiangyang Zhu, Shanghai (CN); Fengxue Zhang, Shanghai (CN); Mingqing Cai, Shanghai (CN); Lei Zhang, Shanghai (CN); Shi Chen, Shanghai (CN); Ling Yu, Shanghai (CN)

(73) Assignee: HUABO BIOPHARM (SHANGHAI) CO., LTD., Shanghai (CN)

( * ) Notice: Subject to any disclaimer, the term of this patent is extended or adjusted under 35 U.S.C. 154(b) by 915 days.

(21) Appl. No.: 17/295,394

(22) PCT Filed: Mar. 31, 2020

(86) PCT No.: PCT/CN2020/082535
§ 371 (c)(1),
(2) Date: May 19, 2021

(87) PCT Pub. No.: WO2020/200210
PCT Pub. Date: Oct. 8, 2020

(65) Prior Publication Data
US 2022/0002418 A1   Jan. 6, 2022

(30) Foreign Application Priority Data

Apr. 1, 2019  (CN) .......................... 201910258153.9

(51) Int. Cl.
| | | |
|---|---|---|
| *C07K 16/28* | (2006.01) | |
| *A61K 47/68* | (2017.01) | |
| *A61P 35/00* | (2006.01) | |
| *C07K 16/22* | (2006.01) | |
| *A61K 39/00* | (2006.01) | |

(52) U.S. Cl.
CPC ...... *C07K 16/2827* (2013.01); *A61K 47/6879* (2017.08); *A61P 35/00* (2018.01); *C07K 16/22* (2013.01); *A61K 2039/505* (2013.01); *C07K 2317/31* (2013.01); *C07K 2317/92* (2013.01)

(58) Field of Classification Search
CPC ................ C07K 16/2827; C07K 16/22; C07K 2317/31; C07K 2317/92; C07K 14/705; C07K 2319/33; C07K 2317/565; A61K 47/6803; A61K 47/6879; A61K 2039/505; A61P 35/00; G01N 33/574; C12N 15/62
See application file for complete search history.

(56) References Cited

FOREIGN PATENT DOCUMENTS

| | | | | |
|---|---|---|---|---|
| CN | 105175545 A | 1/2019 | | |
| CN | 109942712 A | 6/2019 | | |
| WO | 2015000181 A1 | 8/2015 | | |
| WO | WO-2018035084 A1 | * 2/2018 | ............. | A61K 45/06 |
| WO | 2020114355 A1 | 6/2020 | | |

OTHER PUBLICATIONS

Zhang, X et. al. "Inhibition of autophagy potentiated the anti-tumor effects of VEGF and CD47 bispecific therapy in glioblastoma", 2018, Applied Microbiology and Biotechnology, 102, 6503-6513. (Year: 2018).*
International Search Report mailed Jun. 28, 2020 corresponding to PCT/CN2020/082535 filed Mar. 31, 2020; 3 pages.

* cited by examiner

*Primary Examiner* — Nelson B Moseley, II
*Assistant Examiner* — Alyssa Rae Stonebraker
(74) *Attorney, Agent, or Firm* — Mintz Levin Cohn Ferris Glovsky and Popeo, P.C.

(57) ABSTRACT

The present invention provides an anti-PD-L1/VEGF bispecific antibody and a use thereof. Specifically, the present invention provides a bifunctional antibody, comprising: (a) anti-PD-L1 antibody or element; and (b) an anti-VEGF antibody or element linked to the anti-PD-L1 antibody or element. The bifunctional antibody of the present invention can simultaneously bind to VEGF and PD-L1, thereby exerting a therapeutic effect on VEGF and PD-L1-positive tumor cells (especially malignant tumor cells).

12 Claims, 4 Drawing Sheets
Specification includes a Sequence Listing.

ANTI-PD-L1/VEGF BIFUNCTIONAL ANTIBODY AND USE THEREOF

RELATED APPLICATION

This application is U.S. national stage application under 35 U.S.C. § 371 of International Patent Application No. PCT/CN2020/082535, filed on Mar. 31, 2020, which claims priority to Chinese Patent Application No. 201910258153.9, filed on Apr. 1, 2019.

REFERENCE TO SEQUENCE LISTING

The instant application contains a Substitute Sequence Listing, which has been filed electronically in ASCII format and is hereby incorporated by reference in its entirety. Said ASCII copy, created on May 13, 2021, is named WO2020200210A1.Sequence listing.txt and is 18,897 bytes in size.

TECHNICAL FIELD

The invention relates to the field of tumor immunology, and in particular to an anti-PD-L1/VEGF bifunctional antibody and use thereof.

BACKGROUND

Tumors can be divided into two categories of benign tumors and malignant tumors according to the cell characteristics of new organisms and the degree of damage to the body. Among them, malignant tumor disease is a major disease that endangers human health in today's society, with the second highest lethality. Common tumors include liver cancer, lung cancer, gastric cancer, breast cancer, and bladder cancer. According to reports, in 2018, there were approximately 18.1 million new cancer cases and 9.6 million cancer deaths worldwide (17 million and 9.5 million respectively after excluding non-melanoma skin cancer). Among the 18.1 million new cancer cases, cases in Asia accounted for nearly half, and among the 9.6 million cancer deaths, cases in Asia accounted for nearly 70%.

Due to individual differences of malignant tumors, most patients are generally treated comprehensively, that is, combined with surgery, chemotherapy, radiotherapy, immunotherapy, traditional Chinese medicine treatment, interventional therapy, microwave therapy, etc., in order to greatly increase the cure rate and improve the quality of life of patients. Immunotherapy refers to the treatment method for the body's low or hyperactive immune status, thereby artificially enhancing or inhibiting the body's immune function to achieve the purpose of curing diseases. There are many methods for immunotherapy, suitable for treatment of various diseases. Tumor immunotherapy is a treatment method aimed at activating the human immune system, relying on autoimmune function to kill cancer cells and tumor tissues, thereby controlling and eliminating tumors. Unlike previous surgery, chemotherapy, radiotherapy, and targeted therapy, the target of immunotherapy is not tumor cells or tissues, but the body's own immune system. It includes monoclonal antibody immune checkpoint inhibitors, therapeutic antibodies, cancer vaccines, cell therapy and small molecule inhibitors and so on. In recent years, the good news of tumor immunotherapy has continued. At present, it has shown strong anti-tumor activity in the treatment of solid tumors such as melanoma, non-small cell lung cancer, kidney cancer and prostate cancer. A number of tumor immunotherapy drugs have been approved by the US FDA (Food and Drug Administration, FDA) for clinical application.

Most of the current antibody drugs on the market are monoclonal antibodies. Therapeutic monoclonal antibodies have been used to treat cancer, autoimmune diseases, inflammation and other diseases, and most of them are specific to one target. However, patients undergoing monoclonal antibody therapy may develop drug resistance or non-response. In addition, some diseases have multiple influencing factors in the body, including different signaling pathways, different cytokines and receptor regulation mechanisms, and so on. Single-target immunotherapy does not seem to be enough to destroy cancer cells. Therefore, it is necessary to be achieved by combining different drugs or multiple targeting strategies using a multispecific antibody.

Although bifunctional antibodies are the direction of antibody drug research and development, they face many challenges, such as preclinical evaluation models, low expression levels, poor stability, complex processes, and large differences in quality control. Therefore, the development of bifunctional antibodies has been difficult.

Therefore, it is urgent in the art to develop an anti-tumor bispecific antibody with good specificity, good efficacy and easy preparation.

SUMMARY OF THE INVENTION

It is an object of the present invention to provide an anti-tumor bispecific antibody with stable structure, good specificity and easy preparation.

In a first aspect of the invention, it provides a bifunctional antibody, wherein the bifunctional antibody comprises:
  (a) an anti-PD-L1 antibody or element;
  (b) an anti-VEGF antibody or element linked to the anti-PD-L1 antibody or element.

In another preferred embodiment, the anti-PD-L1 antibody or element and the anti-VEGF antibody or element are linked with a linker peptide.

In another preferred embodiment, the linker peptide comprises an antibody constant region sequence.

In another preferred embodiment, the anti-VEGF antibody or element is linked to a region of the anti-PD-L1 antibody, and the region is selected from the group consisting of: heavy chain variable region, heavy chain constant region, light chain variable region, and a combination thereof.

In another preferred embodiment, the anti-VEGF antibody or element is linked to the initiation terminal of the heavy chain variable region of the anti-PD-L1 antibody.

In another preferred embodiment, the anti-VEGF antibody or element is linked to the termination of the heavy chain constant region of the anti-PD-L1 antibody.

In another preferred example, the anti-PD-L1 antibody or element is linked to a region of the anti-VEGF antibody, and the region is selected from the group consisting of: heavy chain variable region, heavy chain constant region, light chain variable region, and a combination thereof.

In another preferred embodiment, the anti-PD-L1 antibody or element is linked to the initiation terminal of the heavy chain variable region of the anti-VEGF antibody.

In another preferred embodiment, the anti-PD-L1 antibody or element is linked to the termination of the heavy chain constant region of the anti-VEGF antibody.

In another preferred embodiment, the element comprises an extracellular region of a ligand, a receptor or a protein.

In another preferred embodiment, the anti-PD-L1 antibody is selected from the group consisting of a nanobody, a single chain antibody, and a double chain antibody.

In another preferred embodiment, the anti-PD-L1 antibody is selected from the group consisting of an animal-derived antibody (such as a murine antibody), a chimeric antibody and a humanized antibody.

In another preferred embodiment, the humanized antibody comprises a fully humanized antibody.

In another preferred embodiment, the anti-PD-L1 element comprises an extracellular region of a PD-L1 receptor (such as PD-1) or a protein.

In another preferred embodiment, the anti-VEGF antibody is selected from the group consisting of a nanobody, a single chain antibody, and a double chain antibody.

In another preferred embodiment, the anti-VEGF antibody is selected from the group consisting of an animal-derived antibody (such as a murine antibody), a chimeric antibody and a humanized antibody.

In another preferred embodiment, the anti-VEGF element comprises an extracellular region of a VEGF receptor (such as VEGFR) or a protein.

In another preferred embodiment, the anti-VEGF antibody or element is in a monovalent form or a polyvalent form (such as a bivalent form).

In another preferred embodiment, the amount of anti-VEGF antibody or element in the bifunctional antibody is 1-6, preferably is 1-4.

In another preferred embodiment, the bifunctional antibody is a homodimer.

In another preferred embodiment, the bifunctional antibody has a structure shown in formula I from the N-terminal to the C-terminal:

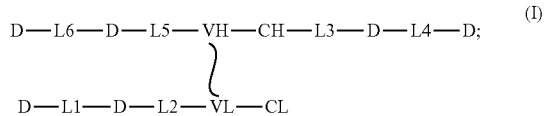

wherein,
each D is independently absent or the anti-VEGF antibody or element, and at least one D is the anti-VEGF antibody or element; L1, L2, L3, L4, L5 or L6 is independently a peptide bond or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide or covalent bond;
"-" represents a peptide bond;
wherein, the bifunctional antibody has an activity of simultaneous binding PD-L1 and VEGF.

In another preferred embodiment, each D in formula I is independently absent or the anti-VEGF element, and at least one D is the anti-VEGF element.

In another preferred embodiment, the linker element can be identical or different.

In another preferred embodiment, the L1, L2, L3, L4, L5 or L6 is independently selected from GS, GGGGS (SEQ ID NO 14), GGGGSGGGS (SEQ ID NO 15) and GGSGGSGSGGSGS (SEQ ID NO 16).

In another preferred embodiment, the heavy chain variable region (VH) of the anti-PD-L1 antibody comprises the following three complementary determining regions or CDRs:
CDR1 as shown in SEQ ID NO: 3,
CDR2 as shown in SEQ ID NO: 4, and
CDR3 as shown in SEQ ID NO: 5; and/or
the light chain variable region (VL) of the anti-PD-L1 antibody comprises the following three complementary determining regions or CDRs:
CDR1' as shown in SEQ ID NO: 6,
CDR2' with an amino acid sequence of GIS, and
CDR3' as shown in SEQ ID NO: 7.

In another preferred embodiment, the heavy chain variable region (VH) of the anti-PD-L1 antibody has an amino acid sequence as shown in SEQ ID NO: 1 or 8.

In another preferred embodiment, the light chain variable region (VL) of the anti-PD-L1 antibody has an amino acid sequence as shown in SEQ ID NO: 2 or 9.

In another preferred embodiment, the anti-VEGF element comprises a second extracellular region D2 (VEGFR1D2) of vascular endothelial growth factor 1 (VEGFR1).

In another preferred embodiment, the anti-VEGF element has an amino acid sequence as shown in SEQ ID NO: 10.

In another preferred embodiment, the bifunctional antibody is a double chain antibody.

In another preferred embodiment, the bifunctional antibody has a heavy chain (H chain) and a light chain (L chain).

In another preferred embodiment, the H chain of the bifunctional antibody has an amino acid sequence as shown in SEQ ID NO: 11 or SEQ ID NO: 12.

In another preferred embodiment, the L chain of the bifunctional antibody has an amino acid sequence as shown in SEQ ID NO: 13.

In another preferred embodiment, the antibody is in the form of a drug conjugate.

In another preferred embodiment, the bifunctional antibody also contains (preferably couples) a detectable marker, a targeted marker, a drug, a toxin, a cytokine, a radionuclide, an enzyme, or a combination thereof.

In another preferred embodiment, the bifunctional antibody is coupled to a conjugate of tumor targeted marker.

In another preferred embodiment, the bifunctional antibody further comprises an active fragment and/or a derivative of the bifunctional antibody, wherein the active fragment and/or the derivative retains 70-100% (such as 70%, 75%, 80%, 85%, 90%, 95%, 96%, 97%, 98%, 99%, 100%) anti-PD-L1 activity and 70-100% anti-VEGF activity of the bifunctional antibody.

In another preferred embodiment, the derivative of the antibody has a sequence identity of at least 85% of the antibody of the present invention.

In another preferred embodiment, the derivative of the antibody is a sequence which is obtained through deletion, addition, and/or substitution of one or more amino acids and maintains at least 85% identity.

In another preferred embodiment, the antibody derivative has a sequence identity of at least 86%, 87%, 88%, 89%, 90%, 91%, 92%, 93%, 94%, 95%, 96%, 97%, 98%, 99% of the antibody of the present invention.

In another preferred embodiment, the substitution is conservative substitution.

In another preferred embodiment, the bifunctional antibody has a structure shown in formula Ia or Ib from the N-terminal to the C-terminal:

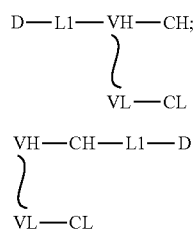

wherein,
D is the anti-VEGF element;
L1 is absent or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide bond;
"-" represents a peptide bond;
wherein, the bifunctional antibody has an activity of simultaneous binding PD-L1 and VEGF.

In another preferred embodiment, the VH comprises CDR1 as shown in SEQ ID NO: 3, CDR2 as shown in SEQ ID NO: 4, and CDR3 as shown in SEQ ID NO: 5.

In another preferred embodiment, the VL comprises CDR1' as shown in SEQ ID NO: 6, CDR2' with an amino acid sequence of GIS, and CDR3' as shown in SEQ ID NO: 7.

In another preferred embodiment, the heavy chain variable region (VH) of the anti-PD-L1 antibody has an amino acid sequence as shown in SEQ ID NO: 1 or 8.

In another preferred embodiment, the light chain variable region (VL) of the anti-PD-L1 antibody has an amino acid sequence as shown in SEQ ID NO: 2 or 9.

In a second aspect of the invention, it provides an isolated polynucleotide encoding the bifunctional antibody of the first aspect of the invention.

In another preferred embodiment, the polynucleotide has a polynucleotide encoding the L chain of the bifunctional antibody.

In another preferred embodiment, the polynucleotide has a polynucleotide encoding the H chain of the bifunctional antibody.

In another preferred embodiment, in the polynucleotide, the ratio of the polynucleotide encoding the L chain to the polynucleotide encoding the H chain is 1:1.

In a third aspect of the invention, it provides a vector comprising the polynucleotide of the second aspect of the invention.

In another preferred embodiment, the vector also comprises all of the polynucleotides in the second aspect of the present invention.

In another preferred embodiment, the vector respectively comprises one polynucleotide in the second aspect of the present invention.

In another preferred embodiment, the vector is an expression vector.

In another preferred embodiment, the vector comprises a plasmid, a phage, a yeast plasmid, a plant cell virus, a mammalian cell virus such as an adenovirus, a retrovirus, or other vectors.

In a fourth aspect of the invention, it provides a genetically engineered host cell comprising the vector of the third aspect of the invention or having the polynucleotide of the second aspect of the invention integrated in the genome.

In a fifth aspect of the invention, it provides a method for preparing the antibody of the first aspect of the invention, comprising the steps of:
(i) culturing the host cell of the fourth aspect of the present invention under suitable conditions, thereby obtaining a mixture containing the bifunctional antibody of the first aspect of the invention; and
(ii) purifying and/or isolating the mixture obtained in step (i), thereby obtaining the bifunctional antibody of the first aspect of the invention.

In another preferred embodiment, the target antibody can be obtained by purification and isolation with protein A affinity column.

In another preferred embodiment, the purity of the target antibody after purification and isolation is greater than 95%, greater than 96%, greater than 97%, greater than 98%, or greater than 99%, preferably is 100%.

In a sixth aspect of the invention, it provides a pharmaceutical composition, comprising:
(I) the bifunctional antibody of the first aspect of the invention; and
(II) a pharmaceutically acceptable carrier.

In another preferred embodiment, the pharmaceutical composition also comprises an additional anti-tumor agent.

In another preferred embodiment, the pharmaceutical composition is a unit dosage form.

In another preferred embodiment, the anti-tumor agent comprises taxol, doxorubicin, cyclophosphamide, Axitinib, Lenvatinib or Pembrolizumab.

In another preferred embodiment, the anti-tumor agent can be individually present in a separate package with the bifunctional antibody, or the anti-tumor agent can be coupled to the bifunctional antibody.

In another preferred embodiment, the dosage form of the pharmaceutical composition comprises a dosage form for gastrointestinal administration or a dosage form for parenteral administration.

In another preferred embodiment, the dosage form for parenteral administration comprises intravenous injection, intravenous drip, subcutaneous injection, topical injection, muscle injection, intratumor injection, intraperitoneal injection, intracranial injection, or intra-cavity injection.

In a seventh aspect of the invention, it provides an immunoconjugate, comprising:
(a) the bifunctional antibody of the first aspect of the invention; and
(b) a coupling moiety, selected from the group consisting of a detectable label, a drug, a toxin, a cytokine, a radionuclide, an enzyme, and a combination thereof.

In another preferred embodiment, the coupling moiety is selected from the group consisting of a fluorescent or luminescent marker, a radioactive marker, MRI (magnetic resonance imaging) or CT (electronic computer X-ray tomography technique) contrast agent, or an enzyme capable of producing a detectable product, a radionuclide, a biotoxin, a cytokine (such as IL-2, etc.), an antibody, an Fc fragment of an antibody, an scFv fragment of an antibody, a gold nanoparticle/nanorod, a viral particle, a liposome, a magnetic nanoparticle, a prodrug activating enzyme (such as DT-diaphorase (DTD) or biphenyl hydrolase-like protein (BPHL)), chemotherapeutic agent (such as cisplatin) and any form of nanoparticles, and the like.

In another preferred embodiment, the antibody moiety is coupled to the coupling moiety via a chemical bond or linker.

In an eighth aspect of the invention, it provides a use of the bifunctional antibody of the first aspect of the invention or the immunoconjugate of the seventh aspect of the invention for preparing (a) a detection reagent or kit and/or (b) preparing a pharmaceutical composition for preventing and/or treating cancer or tumors.

In another preferred embodiment, the tumor is selected from the group consisting of hematological tumors, solid tumors, and a combination thereof.

In another preferred embodiment, the tumor is selected from the group consisting of ovarian cancer, colon cancer, rectal cancer, melanoma (such as metastatic malignant melanoma), renal cancer, bladder cancer, breast cancer, liver cancer, lymphoma, hematological malignancies, head and neck cancer, glioma, gastric cancer, nasopharyngeal carcinoma, laryngeal carcinoma, uterine cancer, hysteroma, and osteosarcoma. Examples of other cancers that can be treated with the method of the invention comprise: bone cancer, pancreatic cancer, skin cancer, prostate cancer, skin or intraocular malignant melanoma, uterine cancer, anal cancer, testicular cancer, carcinoma tubae, endometrial cancer, vaginal cancer, vulva cancer, Hodgkin's disease, non-Hodgkin's lymphoma, esophageal cancer, small intestinal cancer, carcinoma of the endocrine system, thyroid cancer, parathyroid cancer, adrenal carcinoma, soft tissue sarcoma, urethral carcinoma, carcinoma of penis, chronic or acute leukemia comprising acute myeloid leukemia, chronic myeloid leukemia, acute lymphocyte leukemia, chronic lymphocyte leukemia, children's solid tumor, lymphocytic lymphoma, bladder cancer, carcinoma of the kidney or ureter, carcinoma of the renal pelvis, central nervous system (CNS) tumor, primary CNS lymphoma, tumor angiogenesis, spinal tumor, glioma of brain stem, pituitary adenoma, Kapoin's sarcoma, skin cancer, squamous-cell carcinoma, T cell lymphoma, environmentally induced cancer comprising asbestos-induced cancer, and combinations of cancer.

In another preferred embodiment, the tumor is rectal cancer, non-small cytotic lung cancer, melanoma, bladder cancer, or a combination thereof.

In another preferred embodiment, the tumor is a tumor having a high expression of PD-L1 and/or VEGF.

In another preferred embodiment, the medicament or preparation is used for the preparation of a medicament or preparation for preventing and/or treating a disease associated with PD-L1 and/or VEGF (positive expression).

In another preferred embodiment, the antibody is in the form of a drug conjugate (ADC).

In another preferred embodiment, the detection reagent or kit is used for diagnosing a disease associated with PD-L1 and/or VEGF.

In another preferred embodiment, the detection reagent or kit is used for detecting PD-L1 and/or VEGF proteins in a sample.

In another preferred embodiment, the detection reagent is a detecting strip.

In a ninth aspect of the invention, it provides a CAR construct, wherein the antigen binding region of the CAR construct comprises a binding region specifically binding to PD-L1 and a binding region specifically binding to VEGF, and the binding region specifically binding to PD-L1 has a heavy chain variable region and a light chain variable region, wherein the heavy chain variable region comprises CDR1 as shown in SEQ ID NO: 3, CDR2 as shown in SEQ ID NO: 4, and CDR3 as shown in SEQ ID NO: 5;

the VL comprises CDR1' as shown in SEQ ID NO: 6, CDR2' with an amino acid sequence of GIS, and CDR3' as shown in SEQ ID NO: 7.

In another preferred embodiment, the binding region specifically binding to VEGF comprises a second extracellular region D2 (VEGFR1D2) of vascular endothelial growth factor 1 (VEGFR1).

In another preferred embodiment, the binding region specifically binding to VEGF has an amino acid sequence as shown in SEQ ID NO: 10.

The present invention also provides a nucleic acid sequence encoding the CAR construct.

The present invention also provides a vector comprising the nucleic acid sequence encoding the CAR construct.

In a tenth aspect of the present invention, it provides a recombinant immune cell expressing an exogenous CAR construct, which is the CAR construct of the ninth aspect of the present invention.

In another preferred embodiment, the immune cell is selected from the group consisting of an NK cell, a T cell, an NKT cell, and a combination thereof.

In another preferred embodiment, the immune cell is derived from human or non-human mammals (such as mice).

The present invention also provides a method for treating a tumor, comprising the step of administering a safe and effective amount of the bifunctional antibody of the first aspect of the invention, or the pharmaceutical composition of the sixth aspect of the invention, or the immunoconjugate of the seventh aspect of the invention, or the immune cell of the tenth aspect of the invention, or a combination thereof.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

MODES FOR CARRYING OUT THE PRESENT INVENTION

Figure 1:
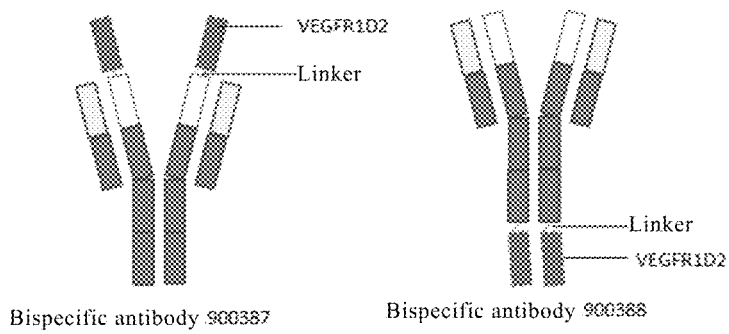
FIG. 1 shows the structural maps of the bifunctional antibodies 900387 and 900388.

Through extensive and intensive research, the inventors have unexpectedly obtained a bifunctional antibody, which is composed of anti-PD-L1 antibody and anti-VEGF nanobody in tandem. Preferably, the bifunctional antibody of the present invention is a homodimer. In vitro experiments confirmed that the bifunctional antibody of the present invention can simultaneously bind to PD-L1 and VEGF, thereby exerting a therapeutic effect on PD-L1 and/or VEGF positive tumor cells (especially malignant tumor cells). Therefore, the bifunctional antibody of the present invention can be developed as an effective antitumor drug. The present invention is completed by the inventors on this basis.

Terms

In order to understand the present invention more easily, some techniques and scientific terms are specifically defined below. Unless otherwise defined herein, all other technical and scientific terms used herein have the same meaning as commonly understood by the general skilled in the art to which the present invention belongs.

The three-letter code and the mono-letter code of amino acids used in the present invention are described in J. Biol. Chem, 243, P3558 (1968).

As used herein, the term "administration" and "treatment" refer to applying an exogenous drug, therapeutic agent, diagnostic agent or composition to an animal, a human, a subject, a cell, a tissue, an organ, or biofluid. "Administration" and "treatment" can refer to treating, pharmacokinetics, diagnosis, research and experimental methods. The treatment of cells comprises contacts of reagents with cells, as well as contacts of reagents with fluids and contacts of fluids with cells. "Administration" and "treatment" also refer to in vitro and ex-vivo treatment by reagents, diagnosis, binding compositions or by another type of cells. When "treatment" is applied to human, animals or study subjects, it refers to therapeutic treatment, prevention or preventive measures, research and diagnosis, which comprises contacting the anti-human PD-L1 antibodies with people or animals, subjects, cells, tissues, physiological compartment or physiological fluid.

As used herein, the term "treating" refers to administration of a patient with a therapeutic agent for internal or external use, and the agent comprises any of the anti-human PD-L1 antibody and a composition thereof of the present invention, wherein the patient has one or more disease symptoms and the therapeutic agent is known to have a therapeutic effect on these symptoms. Typically, patients are given an amount of therapeutic agent that is effective in relieving the symptoms of one or more diseases (therapeutically effective amount).

As used herein, the term "optional" or "optionally" means that the event or situation described later can occur but does not necessarily occur. For example, "optionally comprising 1-3 antibody heavy chain variable regions" means that there can be, but does not have to be, one, two, or three antibody heavy chain variable regions of a particular sequence.

The "sequence identity" of the present invention means that the degree of identity between two nucleic acids or two amino acid sequences in the presence of an appropriate mutation of substitution, insertion or deletion for optimal alignment and comparison. The sequence identity between the sequence of the present invention and a sequence with identity thereof may be at least 85%, 90%, or 95%, preferably at least 95%. Non-limiting examples include 85%, 86%, 87%, 88%, 89%, 90%, 91%, 92%, 93%, 94%, 95%, 96%, 97%, 98%, 99%, and 100%.

Typically, "antibody" is also referred to as "immunoglobulin" which may be a natural or conventional antibody, wherein the two heavy chains are connected to each other through disulfide bonds and each heavy chain is connected to the light chain through disulfide bonds. There are two types of light chains, λ(l) and κ(k). There are five main heavy chain types (or isotype) that determine the functional activity of antibody molecules: IgM, IgD, IgG, IgA and IgE. Each chain contains different sequence domains. The light chain includes two domains or regions, i.e. a variable domain (VL) and a constant domain (CL). The heavy chain includes four domains, a heavy chain variable region (VH) and three constant regions (CH1, CH2, and CH3, which are collectively referred to as CH). Both the variable regions of light chain (VL) and heavy chain (VH) determine identify and specificity of the antigen. The constant domain of the light chain (CL) and the constant region of the heavy chain (CH) impart important biological properties such as antibody chain binding, secretion, transplacental mobility, complement binding, and binding with the Fc receptor (FcR). The Fv fragment is an N-terminal portion of the immunoglobulin Fab fragment and is composed of variable portions of a light chain and a heavy chain. The specificity of the antibody depends on the structure complementary of the antibody binding site to the antigen determination region. The antibody binding site consists of residues from highly variable regions or complementary determining regions (CDRs). Occasionally, residues from non-highly variable or frame regions (FRs) affect the structure of overall domain and in turn affect the binding site. Complementary determining regions or CDRs refer to amino acid sequences that collectively define binding affinity, and specificity of the natural Fv region of natural immunoglobulin binding sites. The light and heavy chains of the immunoglobulin each have three CDRs, which are separately referred to as CDR1-L, CDR2-L, CDR3-L, CDR1-H, CDR2-H, and CDR3-H. Conventional antibody antigen binding sites thus include six CDRs comprising a set of CDRs from each v region of heavy chain and light chain.

As used herein, the term "single domain antibody" and "nanobody" have the same meaning, and refer to the variable region of cloned antibody heavy chain. The construction of a single domain antibody consists only of one heavy chain variable region. The single domain antibody is the smallest antigen-binding fragment with full function. Typically, the antibody with natural deletion of light chain and heavy chain constant regions 1 (CH1) is first obtained, and the variable region of the antibody heavy chain is cloned, and a single domain antibody consisting only of one heavy chain variable region is constructed.

As used herein, the term "variable" means that antibodies are different from each other in terms of sequence in certain parts of variable regions, which is responsible for the binding and specificity of various specific antibodies to their specific antigens. However, the variability is not distributed evenly throughout the variable regions of an antibody. It is concentrated in three segments called complementarity determining regions (CDRs) or hypervariable regions in the light and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Vol. I, pp. 647-669 (1991)). The constant regions are not directly involved in the binding of an antibody to an antigen, however, they exhibit different effector functions, for example, involved in the antibody-dependent cytotoxicities of an antibody.

As used herein, the term "framework region" (FR) refers to the amino acid sequence inserted between the CDRs, i.e, refers to the more conservative portions in the immunoglobulin light chain and heavy chain variable region between different immunoglobulins in a single species. The light chain and heavy chain of the immunoglobulin each has four FRs, called FR1-L, FR2-L, FR3-L, FR4-L and FR1-H, FR2-H, FR3-H, FR4-H, respectively. Accordingly, the light chain variable domain can thus be referred to as (FR1-L)-(CDR1-L)-(FR2-L)-(CDR2-L)-(FR3-L)-(CDR3-L)-(FR4-L) and the heavy chain variable domain can thus be referred to as (FR1-H)-(CDR1-H)-(FR2-H)-(CDR2-H)-(FR3-H)-(CDR3-H)-(FR4-H). Preferably, the FR of the present invention is human antibody FR or a derivative thereof, and the derivative of the human antibody FR is essentially identical to the naturally occurring human antibody FR, i.e. has a sequence identity of 85%, 90%, 95%, 96%, 97%, 98% or 99%.

With the acknowledge of the amino acid sequences of CDRs, those skilled in the art can easily determine the framework regions FR1-L, FR2-L, FR3-L, FR4-L and/or FR1-H, FR2-H, FR3-H, FR4-H.

As used herein, the term "human frame region" is a frame region that substantially same (about 85% or more, specifically is 90%, 95%, 97%, 99% or 100%) as the frame region of the naturally occurring human antibody.

As used herein, the term "monoclonal antibody" or "mAb" refers to an antibody molecule having a single amino acid composition that targets a specific antigen, and is not to be understood to produce the antibody by any particular method. The monoclonal antibody can be produced by a single clone of B cell or hybridoma, but can also be recombinant, i.e. produced by protein engineering.

As used herein, the term "antigen" or "target antigen" is a molecular or portion of a molecule capable of binding by an antibody or antibody-like binding protein. The term further refers to a molecular or portion of a molecule that can be used in animals to produce an antibody capable of binding to the epitope of the antigen. The target antigen can have one or more epitopes. For each target antigen recognized by antibody or antibody-like binding protein, the antibody-like binding protein can compete with the full antibody that recognize target antigen.

As used herein, the term "affinity" is theoretically defined by the equilibrium association between the full antibody and antigen. The affinity of the bifunctional antibody of the present invention can be evaluated or determined by the KD value (dissociation constant) (or other assay), such as by Bio-Layer Interferometry (BLI), measured with the Fortebiored96 instrument.

As used herein, the term "linker" refers to one or more amino acid residues inserted into the immunoglobulin domain to provide sufficient mobility for the domains of light chain and heavy chain to fold into an immunoglobulin with exchange dual variable domains. The linker of the present invention refers to the linker L1, L2, L3, and L4, wherein the linkers of L1 and L4 are used to connect two anti-VEGF antibodies, and L2 is used to connect the heavy chain anti-VEGF antibody dimer and the light chain variable region (VL) of anti-PD-L1 antibody in the bifunctional antibody of the present invention, and L3 is used to connect the light chain anti-VEGF antibody dimer and the heave chain constant region (CH) of anti-PD-L1 antibody in the bifunctional antibody of the present invention Suitable linker examples include single glyglycine (Gly) or serine (Ser) residue. The identification and sequences of the amino acid residues in the linker may vary depending on the type of secondary structural element that needs to be realized in the linker. A preferred linker is as follows:

L1, L2, L3, L4, L5 or L6 are each independently selected from GS, GGGGS (SEQ ID NO 14), GGGGSGGGS (SEQ ID NO 15), and GGSGGSGSGGSGS (SEQ ID NO 16).

Anti-PD-L1 Antibody

The programmed cell death protein (PD-1) is a newly discovered negative costimulatory molecule belonging to the CD28 immunoglobulin superfamily. PD-1 is generally expressed on activated T cells, B cells and myeloid cells, which has two natural ligand, i.e., programmed death ligand-1 (PD-L1) and PD-L2, both belonging to the B7 superfamily and expressed in antigen presenting cells, and PD-L1 is also expressed in a variety of tissues. PD-L1 is an important negative immunoregulatory factor of PD-1, also known as B7-H1. The combination of PD-L1 and PD-1 mediates the co-inhibitory signal of T cell activation, and inhibits T cell activation and proliferation, playing a negative regulatory role similar to CTLA-4, and inducing the apoptosis of T cells. Moreover, studies show that the tumor micro environments can also protect tumor cells from the damage of immune cells, so that tumor cells cannot be recognized and immune escape occurs. Moreover, the tumor micro environment can continuously express PD-L1, resulting in a severe decrease in the immune function of tumor patients.

The Chinese origin scientist Chen Lieping's Lab first found that PD-L1 is highly expressed in tumor tissue, and regulates the function of tumor infiltrating CD8 T cells. Therefore, the immune regulation targeting PD-1/PD-L1 is of great significance in the anti-tumor research. In recent years, the clinical research of a variety of anti-PD-1/PD-L1 antibodies in tumor immunotherapy is developing rapidly. Currently, Pembrolizumab and Nivolumab are approved by FDA for advanced melanoma. Recently, Nivolumab has also been approved by the US FDA for the treatment of advanced squamous non-small cell lung cancer. In addition, MPDL3280A (anti-PD-L1 monoclonal antibody), Avelumab (anti-PD-L1 monoclonal antibody), etc. have also entered multiple advanced clinical studies, covering non-small cell carcinoma, melanoma, bladder cancer, etc.

The sequence of the anti-PD-L1 antibody of the invention can adopt a known antibody or an antibody prepared by conventional methods or developed by screening. Preferably, the anti-PD-L1 antibody of the invention is obtained after screening, wherein the heavy chain variable region comprises CDR1 as shown in SEQ ID NO: 3, CDR2 as shown in SEQ ID NO: 4, and CDR3 as shown in SEQ ID NO: 5; and the VL comprises CDR1' as shown in SEQ ID NO: 6, CDR2' with an amino acid sequence of GIS, and CDR3' as Shown in SEQ ID NO: 7

| Domain | | sequence | |
|---|---|---|---|
| VH | CDR1 | GYAFTGYT | SEQ ID NO 3 |
| | CDR2 | FYPGSGTL | SEQ ID NO 4 |
| | CDR3 | ARHGTGTLMAMDY | SEQ ID NO 5 |
| VL | CDR1' | QSLANSYGNTY | SEQ ID NO 6 |
| | CDR2' | GIS | - |
| | CDR3' | LQGTHQPPT | SEQ ID NO 7 |

Those skilled in the art can also modify or transform the anti-PD-L1 antibody of the present invention by the technology well known in the art, such addition, deletion and/or substitution of one or more amino acid residues, thereby further increasing the affinity or structural stability of the anti-PD-L1 antibody. The results after modification or transformation are obtained by conventional determination methods.

In another preferred embodiment, the heavy chain variable region (VH) of the anti-PD-L1 antibody has an amino acid sequence as shown in SEQ ID NO: 1 or 8 (underlined are amino acid sequences of heavy chain variable region CDR1, CDR2, and CDR3 in order).

(SEQ ID NO: 1)
QVQLQQSGAELVKPGASVKLSCKAS<u>GYAFTGYT</u>IHWVKQRSGLGLEWLGW

<u>FYPGSGTL</u>KYNEKFKDKATLTADKSSSTVYLELSRLTSEDSAVYFC<u>ARHG</u>

<u>TGTLMAMDY</u>WGQGTSVTVSS (SEQ ID NO: 8)
QVQLVQSGAEVKKPGASVKVSCKAS<u>GYAFTGYT</u>IHWVRQAPGQRLEWMGW

<u>FYPGSGTL</u>KYSEKFQGRVTITRDKSLSTAYMELSSLRSEDTAVYYC<u>ARHG</u>

<u>TGTLMAMDY</u>WGQGTLVTVSS

In another preferred embodiment, the light chain variable region (VL) of the anti-PD-L1 antibody has an amino acid sequence as shown in SEQ ID NO: 2 or 9 (underlined are amino acid sequences of light chain variable region CDR1, CDR2, and CDR3 in order).

(SEQ ID NO 2)
DVVVTQTPLSLPVSFGDQVSISCRSS<u>QSLANSYGNTY</u>LSWYLHKPGQSPQ

LLIY<u>GIS</u>NRFSGVPDRFSGSGSGTDFTLKISTIKPEDLGMYYC<u>LQGTHQP</u>

<u>PTF</u>GGGTKLEIK (SEQ ID NO 9)
DVVMTQTPLSLSVTPGQPASISCKSS<u>QSLANSYGNTY</u>LSWYLHKPGQSPQ

LLIY<u>GIS</u>NRFSGVPDRFSGSGSGTDFTLKISRVEAEDVGVYYC<u>LQGTHQP</u>

<u>PTF</u>GQGTKLEIK

The anti-PD-L1 antibody dimer of the present invention can be expressed by HEK293 cells or CHO cells.

The anti-PD-L1 antibody binds to the mammal PD-L1, preferably a human PD-L1.

The binding affinity of the PD-L1 antibody to PD-L1 is 9.40E-10 M, preferably is not less than 5E-09M.

In another preferred embodiment, the anti-PD-L1 antibody of the invention is a humanized antibody.

Anti-VEGF Antibody

Vascular endothelial growth factor is also called VEGF. VEGF protein was successfully purified and identified by scientists from two biotechnology companies in the United States in 1989, and its gene sequence was cloned and determined, proving that VPF and VEGF are the same protein encoded by the same gene. There are six isoforms of VEGF: VEGF-A, -B, -C, -D, and -E. Their molecular weights range from 35 to 44 kDa, and each isotype binds specifically to specific combinations of three "vascular endothelial growth factor receptors" (VEGFR-1, -2, and -3). However, studies have shown that these receptors have different affinities with VEGF family molecules, and VEGFR1 has a relatively high affinity with VEGF family molecules.

VEGF is a highly conserved homologous dimer glycoprotein. Two single chains each with a molecular weight of 24 kDa formed a dimer with disulfide bonds. The monomer decomposed by VEGF is inactive, and the removal of N2 glycosyl has no effect on the biological effect, but it may play a role in cell secretion. Due to the different shearing methods of mRNA, at least 5 protein forms including VEGF121, VEGF145, VEGF165, VEGF185, and VEGF206 are produced, respectively. Wherein, VEGF121, VEGF145 and VEGF165 are secreted soluble proteins that can directly act on vascular endothelial cells, promote the proliferation of vascular endothelial cells and increase vascular permeability. In 1990, Dr. Folkman from Harvard University put forward the famous Folkman theory that tumor tissue growth must rely on neovascularization to provide enough oxygen and nutrients to maintain. Therefore, it is considered to be the basis for the clinical application of VEGF. With reference to patent CN 103319610, the inventors found that the addition of flanking sequences in the second extracellular domain D2 (Domain2) of VEGFR1 has strong VEGF binding activity, and thus developed a class of recombinant fusion protein drugs, such as VEGFR1D2-Fc.

In a preferred embodiment of the invention, VEGFR1D2 is selected as an anti-VEGF element.

(SEQ ID NO 10)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

Preferably, no matter which terminal of the anti-PD-L1 antibody is connected to the VEGFR1D2 of the present invention, two identical VEGFR1D2 are connected by a linker to appear as a dimer.

Bifunctional Antibody (Bispecific Antibody)

Bispecific antibody (bsAb) is an unnatural antibody that can target two different antigens or proteins at the same time, block two different signal pathways, and stimulate specific immune responses. The role of its specificity and bifunctionality is becoming more and more important in tumor immunotherapy, and it has become a research hotspot in antibody engineering treatment of tumors in the world today. Studies have shown that bispecific antibodies mainly mediate the killing of tumors by immune cells in tumor immunotherapy; they bind dual targets, block dual signaling pathways, exert unique or overlapping functions, and can effectively prevent drug resistance; they have strong specificity, targeting and reduced off-target toxicity, as well as effectively reduced treatment costs and other advantages (taken from the antibody circle). Therefore, the use of bispecific antibody drugs can reduce the chance of tumor cell escape, eliminate tumor cells, and improve treatment efficacy.

Bispecific antibodies can be prepared by two-hybridoma cells, chemical coupling, recombinant genes and other means, among which recombinant gene technology has strong flexibility in binding sites and yield. According to incomplete statistics, there are currently more than 60 bispecific antibodies. According to their characteristics and structural differences, the structure of bispecific antibodies mainly includes bispecific antibodies containing an Fc fragment (IgG-like bispecific antibodies with effector function mediated by Fc) and bispecific antibody without Fc fragment (non-IgG-like bispecific antibody, which plays a role through antigen binding and has the advantages of small molecular weight and low immunogenicity). On Dec. 3, 2014, the US FDA approved the market launch of the bispecific antibody Blincyto (Blinatumomab) developed by Amgen for the treatment of acute lymphoblastic leukemia. Blinatumomab is a CD19/CD3 bispecific antibody. Blincyto (Blinatumomab) is the first bispecific antibody approved by the US FDA.

As used herein, the terms "bispecific antibody", "bifunctional antibody", "antibody of the present invention", "dual antibody of the present invention", "dual antibody", and "bifunctional fusion antibody" are used interchangeably and refer to the anti-PD-L1/VEGF bispecific antibody that simultaneously binds to PD-L1 and VEGF.

In the present invention, the bifunctional antibody comprises:
(a) an anti-PD-L1 antibody or element;
(b) an anti-VEGF antibody or element linked to the anti-PD-L1 antibody or element.

In a preferred embodiment, the bifunctional antibody has a structure shown in formula I from the N-terminal to the C-terminal:

$$D-L6-D-L5-VH-CH-L3-D-L4-D; \atop D-L1-D-L2-VL-CL \qquad (I)$$

wherein,
each D is independently absent or the anti-VEGF antibody or element, and at least one D is the anti-VEGF antibody or element;
L1, L2, L3, L4, L5 or L6 is independently a peptide bond or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide or covalent bond;
"-" represents a peptide bond;
wherein, the bifunctional antibody has an activity of simultaneous binding PD-L1 and VEGF.

In a preferred embodiment, the dual antibody of the present invention is formed by the fusion of PD-L1 antibody and VEGR1D2, and has two pairs of symmetrical peptide chains. Each pair of peptide chains contains a light chain (L chain) and a heavy chain (H chain). All peptides chains are connected by disulfide bonds, and any pair of peptide chains has the L chain and H chain structures as shown in formula Ia or Ib from N terminal to C terminal:

$$D-L1-VH-CH; \atop VL-CL \qquad (Ia)$$

$$VH-CH-L1-D \atop VL-CL \qquad (Ib)$$

wherein,
D is the anti-VEGF element (VEGR1D2);
L1 is absent or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide bond;
"-" represents a peptide bond;
wherein, the bifunctional antibody has an activity of simultaneous binding PD-L1 and VEGF.

In formula Ia or formula Ib, a preferred H chain is as shown in SEQ ID NO: 11 or SEQ ID NO: 12, and a preferred L chain is as shown in SEQ ID NO: 13.

H chain: (amino acid sequence when VEGR1D2 in heavy chain variable region)

```
                                        (SEQ ID NO 11)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

GGSGGSGGSGGSGGSQVQLVQSGAEVKKPGASVKVSCKASGYAFTGYTIH

WVRQAPGQRLEWMGWFYPGSGTLKYSEKFQGRVTITRDKSLSTAYMELSS

LRSEDTAVYYCARHGTGTLMAMDYWGQGTLVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKRVEPKSCDKTHTCPPCPAP

EAAGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEAL

HNHYTQKSLSLSPG
```

H chain: (amino acid sequence when VEGR1D2 in heavy chain constant region)

```
                                        (SEQ ID NO 12)
QVQLVQSGAEVKKPGASVKVSCKASGYAFTGYTIHWVRQAPGQRLEWMGW

FYPGSGTLKYSEKFQGRVTITRDKSLSTAYMELSSLRSEDTAVYYCARHG

TGTLMAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPEAAGGPSVFLFPPKP
```

-continued

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGG

GSGGSGGSGGSGGSSDTGRPFVEMYSEIPEIIHMTEGRELVIPCRVTSPN

ITVTLKKFPLDTLIPDGKRIIWDSRKGFIISNATYKEIGLLTCEATVNGH

LYKTNYLTHRQTNT

L chain:

(SEQ ID NO 13)
DVVMTQTPLSLSVTPGQPASISCKSSQSLANSYGNTYLSWYLHKPGQSPQ

LLIYGISNRFSGVPDRFSGSGSGTDFTLKISRVEAEDVGVYYCLQGTHQP

PTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

The two sequences shown in the structural formula Ia or formula Ib are connected by the disulfide bond of the H chain, thereby forming a symmetrical bifunctional antibody structure.

The dual antibody of the present invention includes not only an intact antibody, but also the fragments of the antibody having an immunological activity or a fusion protein formed by the antibody and another sequence. Therefore, the present invention also includes fragments, derivatives and analogs of the antibody. As used herein, the terms "fragments", "derivatives" and "analogs" refer to the polypeptides basically maintaining the same biological function or activity of the antibody of the present invention. The polypeptide fragments, derivatives or analogs of the present invention may be (i) a polypeptide with one or more conservative or non-conservative amino acid residues (preferably the conservative amino acid residues) being substituted, while such substituted amino acid residues may or may not be encoded by genetic code, or (ii) a polypeptide having substituted group(s) in one or more amino acid residues, or (iii) a polypeptide formed by fusion of the matured polypeptide with another compound (such as the compound that prolongs the half-life of the polypeptide, such as polyethylene glycol), or (iv) a polypeptide formed with additional amino acid sequence fused to said polypeptide sequence (such as, leader sequence, secretion sequence, or a sequence or a protein sequence used to purify the polypeptide, or a fusion protein formed with 6His tag). According to the subject application, these fragments, derivatives and analogs are within the scope commonly known by the skilled person.

The dual antibody of the present invention has anti-PD-L1 and anti-VEGF activity, including two antibodies of the above formula I structure. The term also includes variant forms of the antibody comprising two of the above-mentioned structures of formula I, which have the same function as the dual antibody of the present invention. These variant forms include, but are not limited to, deletions of one or more amino acids (typically 1-50, preferably 1-30, more preferably 1-20, most preferably 1-10), insert ions and/or substitutions, and the addition of one or several amino acids (typically at most 20, preferably at most 10, more preferably at most 5) at the C-terminus and/or N-terminus. For example, in the art, the protein's functions are usually unchanged when an amino acids is substituted by a similar or analogous one. Also, for example, the addition of one or several amino acids at the C-terminus and/or the N-terminus will not normally alter the function of the protein. The term also includes active fragments and active derivatives of the dual antibody of the present invention.

The variant forms of the double antibody include homologous sequences, conserved variants, allelic variants, natural mutants, induced mutants, proteins encoded by a DNA capable of hybridizing to the coding DNA of the antibody of the present invention under high or low stringency conditions, and a polypeptide or protein obtained using an antiserum against the antibody of the present invention.

In the present invention, "the conservative variant of the dual antibody of the present invention" refers to a polypeptide formed by substitution of at most 10, preferably at most 8, more preferably at most 5, and most preferably at most 3 amino acids with amino acids having similar or analogous property, as compared to the amino acid sequence of the dual antibody of the present invention. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Coding Nucleic Acid and Expression Vector

The present invention also provides a polynucleotide molecule encoding the antibody or a fragment thereof or a fusion protein thereof. The polynucleotides of the present invention can be in a form of DNA or RNA. DNA forms include cDNA, genomic DNA, or synthetic DNA. DNA can be single-stranded or double-stranded. DNA can be the coding strand or the non-coding strand. The polynucleotides encoding the mature polypeptides of the present invention comprise coding sequences encoding only the mature polypeptide; coding sequences of the mature polypeptide and various additional coding sequences; coding sequences (and optionally additional coding sequences) of the mature polypeptide, and non-coding sequences.

The term "polynucleotide encoding a polypeptide" may include a polynucleotide that encodes the polypeptide, or a polynucleotide that also includes additional coding and/or non-coding sequences.

The nucleic acid (and the combination of nucleic acid) of the present invention can be used to generate the recombinant antibody of the present invention in an appropriate expression system.

The present invention also relates to polynucleotides that hybridize to the sequences as described above and having at least 50%, preferably at least 70%, more preferably at least 80% identical between the two sequences. In particular, the present invention relates to polynucleotides that can hybridize to the polynucleotides of the present invention under stringent conditions. In the present invention, "stringent conditions" means: (1) hybridization and elution at lower ionic strength and higher temperature, such as 0.2×SSC, 0.1% SDS, 60° C.; or (2) hybridization adding a denaturant, such as 50% (v/v) formamide, 0.1% calf serum/0.1% Ficoll, 42° C., or the like; or (3) hybridization only occurs when the identity between the two sequences is at least 90%, more preferably 95% or more. And the polypeptide encoded by the hybridizable polynucleotide has the same biological function and activity as the mature polypeptide.

The whole length of the nucleotide sequence or the fragment thereof of the antibody of the present invention can be obtained via PCR amplification, recombinant method or artificial synthesis. One feasible method is to synthesize relevant sequences by artificial method, especially when the fragment is short in length. Usually, several small fragments are synthesized first, and then are linked together to obtain a fragment with a long sequence. In addition, the sequence coding the heavy chain and the expression label (e.g. 6His) can be fused together to form a fusion protein.

Once a relevant sequence is obtained, the relevant sequence can be obtained in bulk using a recombination method. This is usually carried out by cloning the sequence into a vector, transforming a cell with the vector, and then separating the relevant sequence from the proliferated host cell by conventional methods. The biomolecules (nucleic acids, proteins, etc.) involved in the present invention include biomolecules that exist in an isolated form.

At present, a DNA sequence encoding the protein of the present invention (or fragments thereof, or derivatives thereof) can completely be obtained by chemical synthesis. The DNA sequence can then be introduced into a variety of existing DNA molecules (or, for example, vectors) and cells known in the art. In addition, mutations can also be introduced into the protein sequences of the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell.

Representative examples are: *Escherichia coli, Streptomactinus*, the bacterial cell of *Salmonella typhimurium*; fungal cells such as yeast; insect cells of *Drosophila* S2 or SF9; animal cells of CHO, COS7, 293 cells, etc.

Transformation of host cells with recombinant DNA can be carried out using conventional techniques well known to the skilled in the art. When the host is a prokaryote such as *E. coli*, competent cells capable of absorbing DNA can be harvested after the exponential growth phase and treated with $CaCl_2$, the steps used are well known in the art. Another method is to use $MgCl_2$. If necessary, the transformation can also be carried out by means of electroporation. When the host is a eukaryote, the following DNA transfection methods can be used: calcium phosphate coprecipitation method, conventional mechanical method, such as micro-injection, electroporation, liposome packaging, etc.

The obtained transformants can be cultured by a conventional method to express a polypeptide encoded by a gene of the present invention. According to the host cell used, the medium used in the culture may be selected from a variety of conventional media. And the host cell can be cultured under conditions suitable for the growth of the host cell. After the host cell has grown to an appropriate cell density, the selected promoter is induced by a suitable method (such as temperature conversion or chemical induction) and the cells are cultured for a further period of time.

In the early culture conditions, the expression level of bispecific antibody can reach 3.9 g/L, and the purity is above 97%, and it can metabolize lactic acid well in the culture process.

The recombinant polypeptide in the method above may be included in the cells, or expressed on the cell membrane, or secreted out of the cell. If necessary, the recombinant protein can be separated and purified by various separation methods according to its physical, chemical, and other properties. These methods are well known to those skilled in the art. and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

The dual antibody of the present invention can be used alone, or can be combined or coupled with a detectable marker (for diagnostic purposes), a therapeutic agent, or any combination of these substances.

Detectable markers for diagnostic purposes include, but are not limited to: fluorescent or luminescent markers, radioactive markers, MRI (magnetic resonance imaging) or CT (electronic computer X-ray tomography technique) contrast agents, or enzymes capable of producing a detectable product.

Therapeutic agents that can combined or coupled with the antibody of the invention include but are not limited to: 1. Radionuclides; 2. Biotoxin; 3. Cytokines such as IL-2; 4. Gold nanoparticles/nanorods; 5. Virus particles; 6. Liposomes; 7. Magnetic nanoparticles; 8. Tumor therapeutic agents (e.g. cisplatin) or anti-tumor drugs in any form, and so on.

Pharmaceutical Composition

The invention further provides a composition. Preferably, the composition is a pharmaceutical composition comprising the bispecific antibody of the present invention or an active fragment thereof or a fusion protein thereof, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intravenous injection, intravenous drip, subcutaneous injection, topical injection, muscle injection, intratumor injection, intra-abdominal (such as intraperitoneal) injection, intracranial injection, or intra-cavity injection.

The pharmaceutical composition of the present invention can be directly used for binding a PD-L1 protein molecule or PD-L1, and thus can be used for treating tumors. In addition, other therapeutic agents can also be used simultaneously.

The pharmaceutical composition according to the present invention comprises a safe and effective amount (e.g. 0.001-

99 wt %, preferably 0.01-90 wt %, preferably 0.1-80 wt %) of the nanobody according to the present invention (or a conjugate thereof) and a pharmaceutically acceptable carrier or excipient. Such carriers include, but are not limited to, saline, buffer solution, glucose, water, glycerin, ethanol or the combination thereof. The pharmaceutical preparation should be matched to the method of administration. The pharmaceutical composition of the present invention can be prepared in the form of injection, for example, prepared by a conventional method using physiological saline or an aqueous solution containing glucose and other adjuvants. Pharmaceutical compositions such as injections and solutions are preferably prepared under sterile conditions. The dosage of active ingredient is therapeutically effective amount, for example from about 10 microgram per kilogram body weight to about 50 milligrams per kilogram body weight per day. Further, the polypeptide of the present invention can also be used in combination with the other therapeutic agents.

In the present invention, the bispecific antibody can be used alone, and the dosage regimen can be adjusted to obtain the best objective response. For example, the drug may be administrated in a single dose, or multiple times over a period of time, or the dose may be reduced or increased proportionately according to the urgency of the treatment situation.

When a pharmaceutical composition is used, a safe and effective amount of the immunoconjugate is administered to a mammal, wherein the safe and effective amount is usually at least about 10 micrograms per kilogram of body weight, and in most cases does not exceed about 50 mg/kg body weight, preferably the dose is about 10 micrograms/kg body weight to about 10 mg/kg body weight. Of course, the particular dose should also depend on various factors, such as the route of administration, patient healthy status, which are well within the skills of an experienced physician.

The Main Advantages of the Present Invention Include:
1. The bifunctional antibody of the present invention can simultaneously bind PD-L1 and VEGF, and the binding configuration of the bifunctional antibody and the binding target can be kept unchanged, and the molecule is stable.
2. The bispecific antibody HB0025 of the present invention can specifically bind to recombinant human PD-L1 and recombinant human VEGF165 (KD less than $10^{-5}$M), and has no non-specific electrostatic and hydrophobic binding with non-target molecules. In the preliminary culture conditions, the expression level of bispecific antibody reached 3.9 g/L, and the purity was above 97%.
3. The bifunctional antibody of the present invention has high binding affinity to the binding target, good blocking activity, and exhibits a certain dual-target synergistic effect, which can effectively kill tumor cells (especially tumors with high expression of PD-L1 and VEGF), thereby significantly reducing tumor volume and tumors, treating cancer, especially solid tumors.
4. Compared with a separate anti-PD-L1 antibody (such as HB0023) and an anti-VEGF fusion protein (such as HB002.1T), the bispecific antibody of the present invention has higher binding activity with PD-L1 and/or VEGF. Specifically, the affinity of the bispecific antibody of the present invention with PD-L1 is about 1E-10 mol; and the affinity with VEGF165 is about 1E-11 mol.
5. The preparation method of the present invention is simple and feasible. The anti-VEGF/PD-L1 bispecific antibody applied by the present invention will have a good application prospect.

The present invention will be further illustrated below with reference to the specific examples. It is to be understood that these examples are for illustrative purposes only and are not intended to limit the scope of the invention. For the experimental methods in the following examples, in which the specific conditions are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, the parts and percentage are weight parts and weight percentage.

Unless specified otherwise, the materials or reagents used in the examples are all commercially available products.

Example 1 Construct of Expression Vector, Expression and Purification of Protein for Bifunctional Antibodies 900387 and 900388

Figure 2:
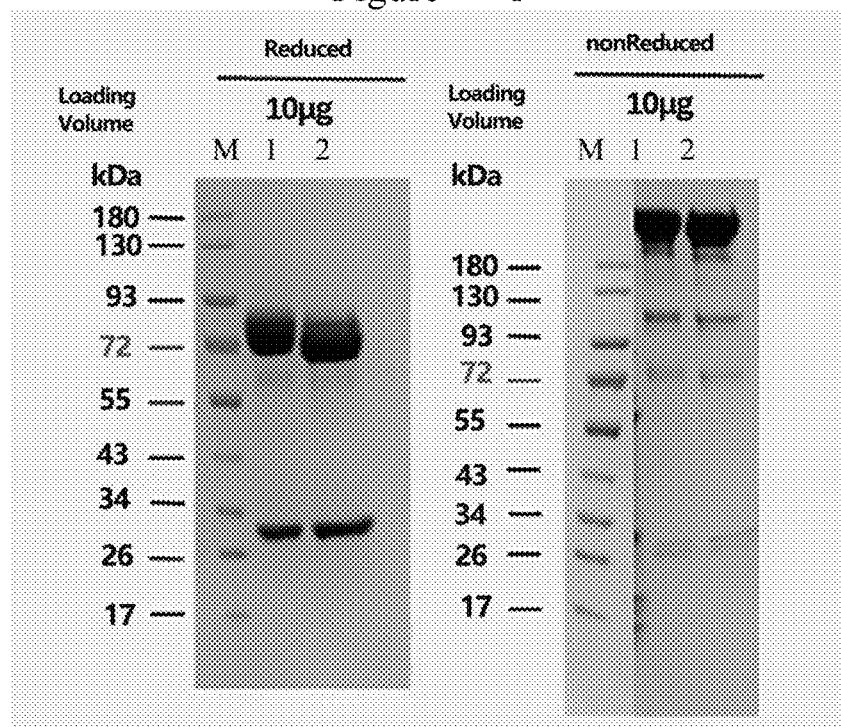
FIG. 2 shows the SDS-PAGE diagrams of the bifunctional antibodies 900387 and 900388. Wherein, lane 1: oxidized or reduced 900387; lane 2: oxidized or reduced 900388.

The anti-PD-L1 antibody of the present invention is a humanized monoclonal antibody (900339) obtained by humanizing a mouse monoclonal antibody (wherein the heavy chain variable region and light chain variable region sequences are as shown in SEQ ID NO: 1 and SEQ ID NO:2, respectively) which was obtained by immunizing mice with human PD-L1-His protein and then screening. The heavy chain sequence is as shown in SEQ ID NO: 8, and the light chain sequence is as shown in SEQ ID NO: 9. The artificially synthesized VEGFR1D2 (the sequence is as shown in SEQ ID NO: 10) is connected to the 5' terminal or 3' terminal of the heavy chain expression vector through a linker (GGSGGSGGSGGSGS, SEQ ID NO: 16), and is co-transfected with the light chain vector (1:1) into CHO-S cells. After culturing for 7 days at 37 degrees, 5% $CO_2$, 130 rpm/min, the supernatant was collected by centrifugation. The supernatant was centrifuged for 10 min at 4000 rpm, and filtered with 0.45 μm filtration, and the filtrate was collected. After the filtrate was purified by Protein A affinity column, antibodies 900387 and 900388 were obtained, and their structural maps were shown in FIG. 1. After purification, the purity of the proteins was detected by SEC_UPLC, and the purity was more than 98%. SDS-PAGE detection was performed, and the results of SDS-PAGE reduction or non-reduction electrophoresis are shown in FIG. 2.

900339-VH
(underlined are amino acid sequences of heavy chain variable region CDR1, CDR2, and CDR3 in order)
SEQ ID NO: 8
QVQLVQSGAEVKKPGASVKVSCKASGYAFTGYTIHWVRQAPGQRLEWMGW

FYPGSGTLKYSEKFQGRVTITRDKSLSTAYMELSSLRSEDTAVYYCARHG

TGTLMAMDYWGQGTLVTVSS

900339-VL (underlined are amino acid sequences of light chain variable region CDR1, CDR2, and CDR3 in order)
SEQ ID NO: 9
DVVMTQTPLSLSVTPGQPASISCKSSQSLANSYGNTYLSWYLHKPGQSPQ

LLIYGISNRFSGVPDRFSGSGSGTDFTLKISRVEAEDVGVYYCLQGTHQP

PTFGQGTKLEIK

VEGFR1D2
SEQ ID NO: 10
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

Bi-specific antibodies 900387 and 900388 were prepared. Wherein, the protein number of 900387 is HB0025, and the related test results in the following experiments were all expressed as HB0025. Its heavy chain amino acid sequence and light chain amino acid sequence are shown as SEQ ID NO: 11 and SEQ ID NO: 13, respectively.

Example 2 Affinity Detection of Bispecific Antibodies

In the present example, the antibody-antigen binding kinetics and affinity were measured using SPR method.

Materials and Instruments

Recombinant human PD-L1, Sino Biological, 10084-H08H
Recombinant human VEGF165, Sino Biological, 11066-HNAH
Amino Coupling Kit, GE, BR-1000-50
HBS-EP (10×), GE, BR-1006-69
Human Antibody Capture Kit, GE, BR-1008-39
Series S Sensor Chip CM5, GE, BR-1005-30
BIACORE, GE, Biacore 8K Methods: Anti-Human Capture-CM5 chip was prepared according to the amino coupling method of the Human Antibody Capture Kit. The chip was balanced at room temperature for 20-30 min, and then loaded into Biacore 8K instrument. The transient transduced protein was diluted to experimental working concentration with equilibration buffer. The antigen was diluted to 50 nM with equilibration buffer, and then diluted to seven concentration gradients with a 3-fold dilution, and two zero concentrations (equilibration buffer) and one repeat concentration (usually a repeat of the lowest concentration) were set. According to the order of antibody, antigen, and regeneration, cyclical experimental analysis were performed on 10 antigen concentrations (2 zero concentrations, 7 gradient concentrations and 1 repeat concentration), wherein the antigen injection flow rate was 30 μL/min, binding time was 120 seconds, and dissociation time was 600 seconds. After the analysis was completed, the corresponding analysis program was selected to analyze the data, confirming that there was no obvious reference binding. Kinetics, 1:1 binding modle was selected to fit the data, and the kinetic related parameters Ka, Kd and KD values of human-mouse chimeric antibody and humanized antibody were obtained. The affinities of the bispecific antibody HB0025 to recombinant human PD-L1 and recombinant human VEGF165 are shown in Table 1 and Table 2.

TABLE 1

Affinity of the bispecific antibody HB0025 to recombinant human PD-L1

| Antibody | Ka(1/Ms) | Kd(1/s) | KD(M) |
|---|---|---|---|
| HB0025 | 4.762E+05 | 4.018E-04 | 8.438E-10 |

TABLE 2

Affinity of the bispecific antibody HB0025 to recombinant human VEGF165

| Antibody | Ka(1/Ms) | Kd(1/s) | KD(M) |
|---|---|---|---|
| HB0025 | 9.496E+06 | 2.799E-04 | 2.947E-11 |

The results show that the bispecific antibody HB0025 had a good affinity with recombinant human PD-L1; and the bispecific antibody HB0025 had a good affinity with recombinant human VEGF165.

Example 3 Non-Specific Adsorption Effects of Bispecific Antibodies and Non-Target Molecules In the present example, the non-specific adsorption effects of the antibody and the non-target molecules were determined using the SPR method.

Materials and Instruments

Figure 3:
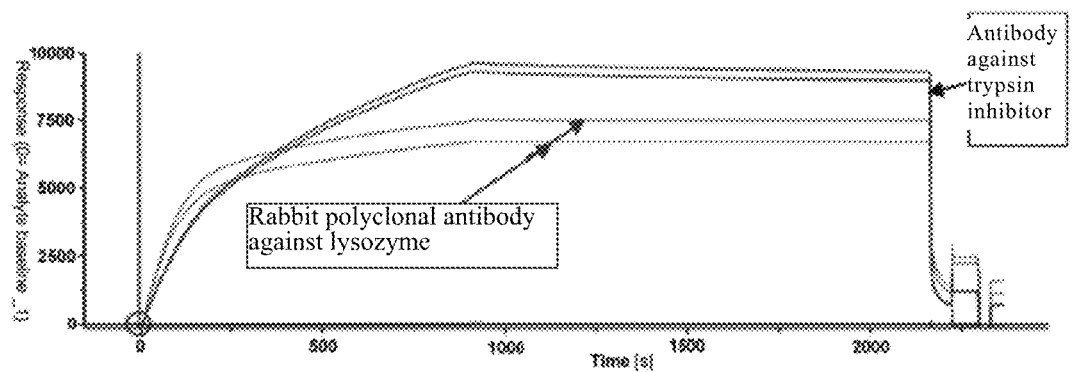
FIG. 3 shows the sensing diagram of detected nonspecific adsorption of bispecific antibody to non-target molecule.

Egg white lysozyme, Sigma, L3790
Soybean trypsin inhibitor 1-S type, Sigma, T-2327
Amino Coupling Kit, GE, BR-1000-50
HBS-EP (10×), GE, BR-1006-69
Rabbit polyclonal antibody against lysozyme, ABcam, Ab391
Antibody against trypsin inhibitor, LifeSpan Biosciences, LS-C76609
0.85% phosphoric acid solution, ProteOn, 176-2260
50 mm hydroxide, ProteOn, 176-2230
Series S Sensor Chip CM5, GE, BR-1005-30
BIACORE, GE, Biacore 8K Methods: Series S Sensor Chip CM5 was balanced at room temperature for 20-30 min, and loaded into Biacore 8K instrument. Egg white lysozyme and soybean trypsin inhibitor 1-S type were fixed to the CM5 chip, respectively, using the Amino Coupling Kit. The injection buffer was HBS-EP+ 1×. 4 balance cycles were settled. The rabbit polyclonal antibody against lysozyme, the antibody against trypsin inhibitor, and the humanized monoclonal antibody were diluted to 1000 nM with equilibration buffer, and the flow rate was set as 5 μL/min, and the injection channels were 1, 2 and 3. The Flow Cells were 1 and 2. The binding time was 10 min, and the dissociation time was 15 min. The regeneration flow rate was 50 μl/min, which is regenerated first with 0.85% phosphoric acid for 60s, and then with 50 mM sodium hydroxide for 30s. The results of non-specific adsorption of bispecific antibody HB0025 and non-target molecules are shown in Table 3, and the sensor diagram of the detection of non-specific adsorption of bispecific antibody and non-target molecules is shown in FIG. 3.

TABLE 3

Detection results of non-specific adsorption of bispecific antibody HB0025 and non-target molecules

| Name | Lysozyme (RU) | Trypsin inhibitor (RU) | Deactivated carboxymethyl glucan (RU) | Carboxymethyl glucan (RU) |
|---|---|---|---|---|
| buffer | 29.9 | 13.6 | 10.7 | 10.1 |
| Polyclonal antibody against lysozyme | 7731.3 | 19 | 16.1 | 15.2 |
| Anti-trypsin inhibitor | 55.5 | 5688 | 24.9 | 15.6 |

TABLE 3-continued

Detection results of non-specific adsorption of bispecific antibody HB0025 and non-target molecules

| Name | Lysozyme (RU) | Trypsin inhibitor (RU) | Deactivated carboxymethyl glucan (RU) | Carboxymethyl glucan (RU) |
|---|---|---|---|---|
| HB0025-22A3/ 9E3-ProA-EP | 32.6 | 14.9 | 10.7 | 10.2 |
| HB0025-22F5/ 4E6-ProA-EP | 34 | 13.6 | 9.8 | 9.6 |

Note:
It is generally believed that after deducting the influence of Buffer, a response value below 20RU is considered as a weak interaction and can be ignored; a response value more than 20RU is considered as an obvious interaction; and a response value more than 100RU is a strong interaction.

According to the results, after deducting the background of the buffer, the binding signals of HB0025 with soybean trypsin inhibitor 1-S type and lysozyme were both less than 20, so it can be considered that the four samples had no non-specific electrostatic and hydrophobic binding. Further, after reducing the antibody into the human body, the immunization of the human body was reduced, thus preventing a series of immune diseases such as hemangioma.

According to the quality control results of egg white lysozyme and soybean trypsin inhibitor 1-S type by rabbit polyclonal antibody against lysozyme and antibody against trypsin inhibitor, respectively, using SPR technology, it can be determined that the egg white lysozyme and soybean trypsin inhibitor fixed to the CM5 chip by amino coupling showed normal activity and maintained well (if the binding signals were all less than 20, it can be considered that the sample had no non-specific electrostatic and hydrophobic binding).

Figure 4:
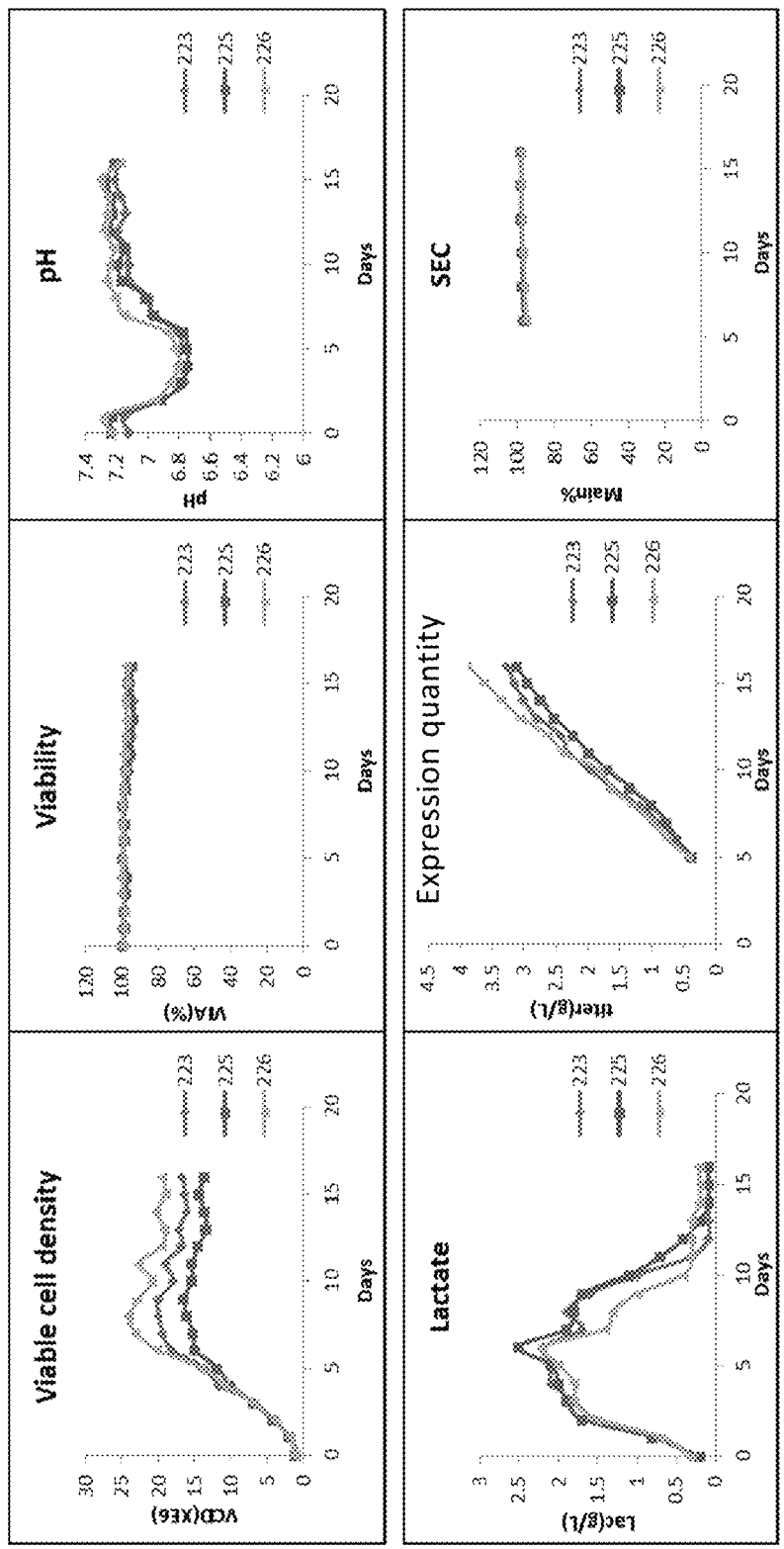
FIG. 4 shows the result of reactor culture, comprising cell density (A), survival rate (B), pH (C), lactic acid metabolism (D), expression quantity (E) and purity (F). Wherein, 223: interval feed, and reducing temperature to 33° C.; 225: interval feed, and reducing temperature to 31° C.; daily feed, and reducing temperature to 31° C.

Example 4 In Vivo Drug Efficacy Detection of Bispecific Antibody 4.1 Preparation of Bispecific Antibody BalanA medium was used and a certain amount of feed was added for culturing. As shown in FIG. 4, the CHO-K1 cell line could metabolize lactic acid very well; the cell growth status was good, and the survival rate was higher than 90% when harvested at 16 days; when the temperature was lowered to 33° C. and 31° C., there was no significant difference in expression, about 3 g/L; daily feeding could significantly increase cell density and expression, and the final expression was 3.9 g/L; the purity in the whole culture process did not decrease, and it was maintained at about 97%.

4.2 In Vivo Pharmacological Experiment Design and Results

In vivo efficacy of HB0025. hCD34+ humanized mouse were inoculated with human lung adenocarcinoma HCC-827 cells in the right armpit. When the tumor grew to an average of about 100-150 mm$^3$, 48 tumor-bearing mice were randomly divided into 6 groups according to the ratio of hCD45+ in the peripheral blood and the tumor volume, 8 animals per group. Via tail vein, G1 group was administrated with PBS, G2 group was administrated with 1 mg/kg of HB0023 (anti-PD-L1 monoclonal antibody, i.e. the humanized monoclonal antibody 900339 in Example 1), G3 group was administrated with 1 mg/kg of HB0025, G4 group was administrated with 3 mg/kg of HB0025, G5 group was administrated with 10 mg/kg of HB0025, G6 group was administrated with 1 mg/kg of HB002.1T (anti-VEGF fusion protein, patent number CN103319610B), respectively. The administration was preformed twice a week, 9 times in total. The tumor volumes and mouse body weights were measured twice a week. During the experiment, when the average tumor volume of the animals in a certain group exceeded 2000 mm$^3$ or the experiment was over, the animals were euthanized and the tumor was weighed.

Figure 5:
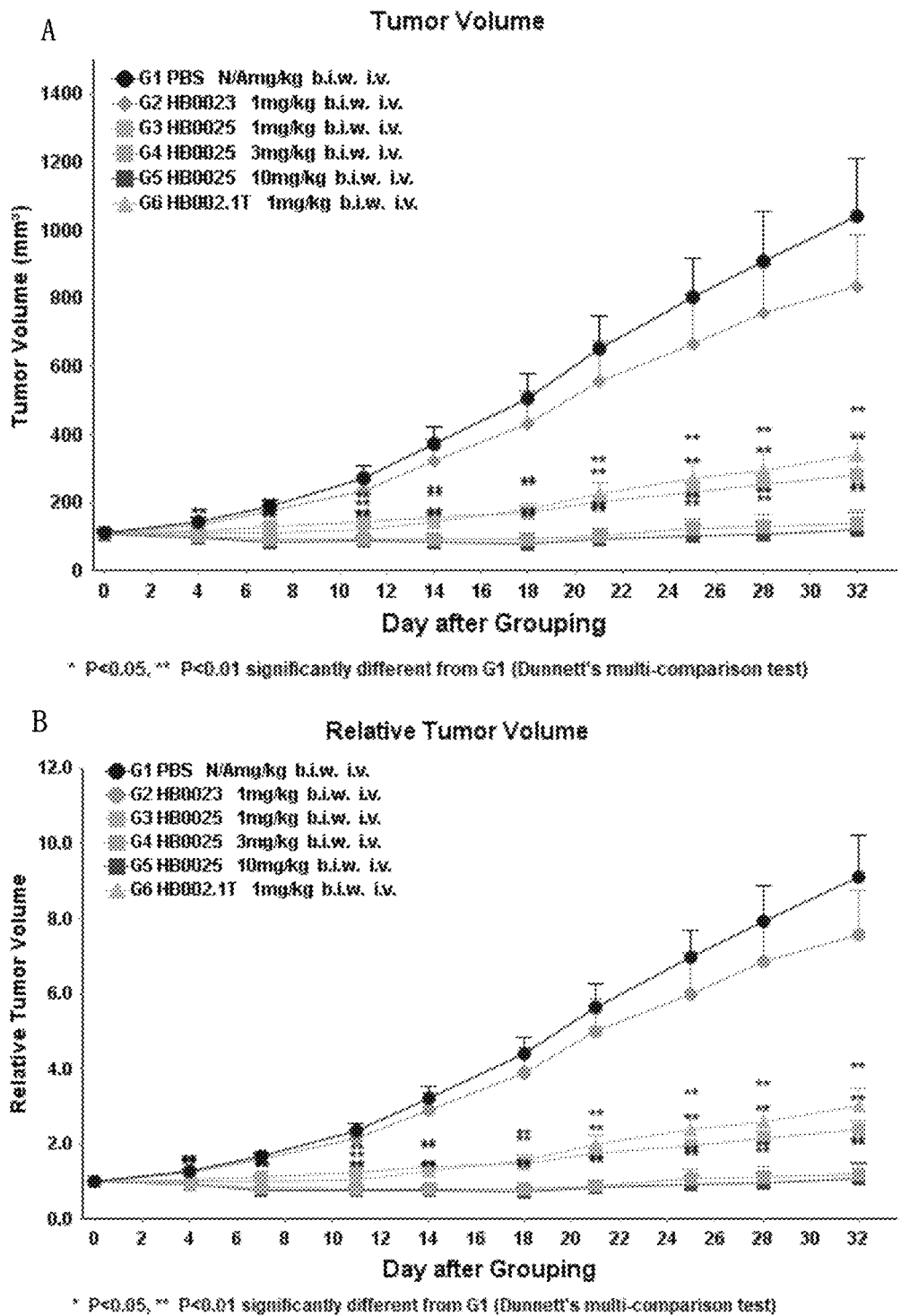
FIG. 5 shows the variation trend of tumor volume (A) and relative tumor volume (B) of animals in each group. Note: the values shown in the figure are the mean tumor volumes of animals in each group ±SEM; b.i.w. means twice a week; i.v. means intravenous injection.
Figure 6:
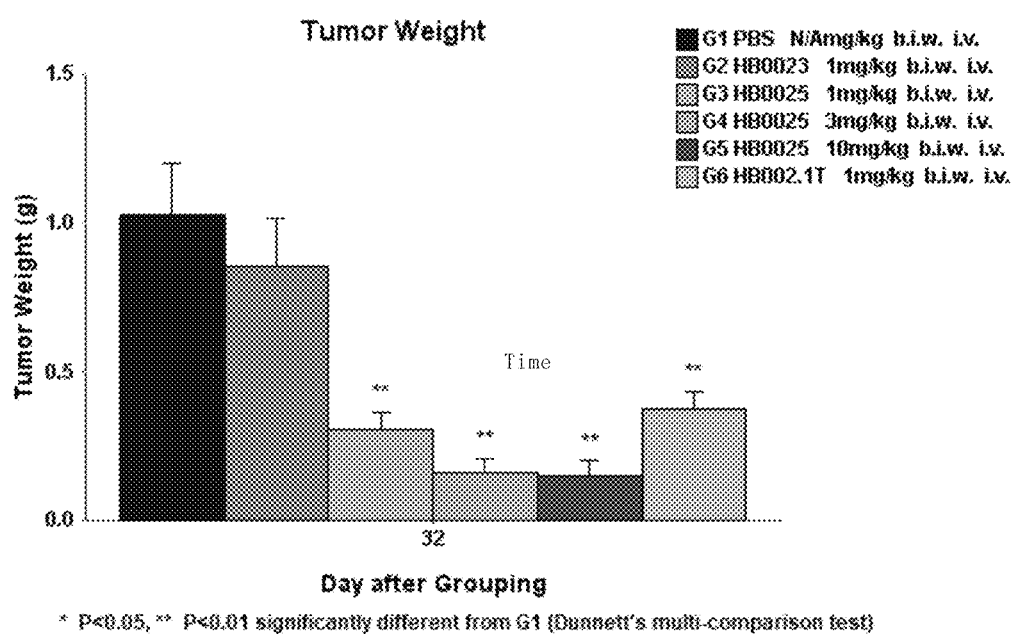
FIG. 6 shows the tumor weight (g) of D32 in each group. Note: the values shown in the figure are mean body weights of animals in each group ±SEM; b.i.w. means twice a week; i.v. means intravenous injection.

During the experiment, the tumor volume of the mice in PBS vehicle control group (G1) continued to increase (see FIG. 5), indicating that the HCC827 lung cancer cell hCD34+ humanized mouse subcutaneously transplanted tumor model was successfully established. G2 animals were administrated with 1 mg/kg of HB0023, and the tumor volume increased relatively slowly after administration. Compared with the vehicle control group in the same period, the tumor volumes and relative tumor volumes were relatively reduced, but there was no statistical difference. At the end of the experiment on the 32nd day, the tumor weights were relatively reduced than those of the vehicle control group ($P>0.05$, see FIG. 5, FIG. 6), and the tumor inhibition rate was 17.48%. G6 animals were administrated with 1 mg/kg of HB002.1T, and the tumor volume increased slowly after administration. Compared with the vehicle control group in the same period, the tumor volumes and relative tumor volumes were significantly reduced ($P<0.05$, see FIG. 5). At the end of the experiment on the 32nd day, the tumor weights were significantly reduced than those of the vehicle control group ($P<0.05$, see FIG. 6), and the tumor inhibition rate was 64.08%.

Animals in G3, G4, and G5 groups were administrated with 1, 3, and 10 mg/kg of HB0025, respectively. After the administration, the tumor volumes increased slowly, and the tumor volumes and relative tumor volumes were significantly lower than those of the vehicle control group in the same period ($p<0.05$). At the end of the experiment on the 32nd day, the tumor weights were significantly reduced than those of the vehicle control group ($P<0.05$, see FIG. 6), and the tumor inhibition rates were 70.87%, 84.47%, and 85.44%, respectively, indicating that HB0025 can effectively inhibit the growth of subcutaneous grafts of lung cancer in hCD34+ humanized mouse HCC827, and the effective tumor suppressor dose is 1 mg/kg.

Compared with the administration of 1 mg/kg of HB0023 and HB002.1T (single target antibody/fusion protein), the tumor volumes, relative tumor volumes, and tumor weights of animals administrated with the same dose of bispecific antibody HB0025 all decreased correspondingly (see FIG. 5 and FIG. 6), showing a certain synergistic effect of dual targets.

Example 5

In the present example, the affinity, the non-specific adsorption with non-target molecules, and the in vivo efficacy of the bispecific antibody 900388 (with heavy chain amino acid sequence and light chain amino acid sequence shown in SEQ ID NO: 12 and SEQ ID NO: 13 respectively) prepared in Example 1 were tested. The experimental methods were the same as those in Examples 2-4, wherein the HB0025 was replaced with the bispecific antibody 900388.

TABLE 4

| | Affinity of bispecific antibody 900388 to PD-L1 and VEGF165 | | | | | |
|---|---|---|---|---|---|---|
| Antigen | Antibody | ka (1/Ms) | kd(1/s) | KD (M) | Kinetics Chi$^2$ (RU$^2$) | tc |
| PD-L1 | 900388 | 6.332E+5 | 5.217E-4 | 8.240E-10 | 0.0876 | 4.464E+7 |
| VEGF165 | 900388 | 1.030E+7 | 4.104E-4 | 3.984E-11 | 1.31 | 1.105E+8 |

The results show that the bispecific antibody 900388 had good affinity to recombinant human PD-L1 and recombinant human VEGF165, had no non-specific electrostatic and hydrophobic binding, and can treat tumors well, significantly reducing animal tumor volume and tumor weight.

The above examples show that the anti-VEGF/PD-L1 bispecific antibody of the present invention can be expressed in CHO-K1 cells and can be further purified by affinity chromatography. The obtained bispecific antibody can bind to PD-L1 positive cells and VEGF positive cells. In addition, the antibody has good affinity, and not only has good anti-VEGF biological activity, but also perfectly retains the biological activity of anti-PD-L1 antibody. Therefore, the anti-VEGF/PD-L1 bispecific antibody of the present invention will have a good application prospect.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A bifunctional antibody, wherein the bifunctional antibody comprises:
   (a) an anti-PD-L1 antibody comprising a heavy chain variable region (VH) and a light chain variable region (VL),
   wherein the VH comprises the following three heavy chain complementary determining regions (HC CDRs):
   HC CDR1 set forth as SEQ ID NO: 3,
   HC CDR2 set forth as SEQ ID NO: 4, and
   HC CDR3 set forth as SEQ ID NO: 5; and
   wherein the VL comprises the following three light chain (LC CDRs):
   LC CDR1 set forth as SEQ ID NO: 6,
   LC CDR2 set forth as GIS, and
   LC CDR3 set forth as SEQ ID NO: 7; and
   (b) an anti-VEGF antibody or element linked to the anti-PD-L1 antibody, and
   wherein the anti-VEGF element comprises an extracellular region of a vascular endothelial growth factor receptor.

2. The bifunctional antibody of claim 1, wherein the bifunctional antibody has a structure shown in formula I from the N-terminal to the C-terminal:

$$D—L6—D—L5—VH—CH—L3—D—L4—D; \atop D—L1—D—L2—VL—CL \quad (I)$$

wherein,
each D is independently absent or the anti-VEGF antibody or element, and at least one D is the anti-VEGF antibody or element;
L1, L2, L3, L4, L5 or L6 is independently a peptide bond or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide or covalent bond;
"-" represents a peptide bond;
wherein, the bifunctional antibody has an activity of simultaneous binding PD-L1 and VEGF.

3. An isolated polynucleotide encoding the bifunctional antibody of claim 1.

4. A vector comprising the polynucleotide of claim 3.

5. A genetically engineered host cell comprising a vector comprising the polynucleotide of claim 3 or having the polynucleotide integrated in the genome.

6. A method for preparing the bifunctional antibody of claim 1, which comprises the step of:
   (i) culturing the host cell of claim 5 under suitable conditions, thereby obtaining a mixture containing the bifunctional antibody of claim 1; and
   (ii) purifying and/or isolating the mixture obtained in step (i), thereby obtaining the bifunctional antibody of claim 1.

7. A pharmaceutical composition, comprising:
   (I) the bifunctional antibody of claim 1; and
   (II) a pharmaceutically acceptable carrier.

8. An immunoconjugate, comprising:
   (a) the bifunctional antibody of claim 1; and
   (b) a coupling moiety selected from the group consisting of a detectable label, a drug, a toxin, a cytokine, a radionuclide, an enzyme, and a combination thereof.

9. A method for treating a tumor, comprising the step of administering the bifunctional antibody of claim 1.

10. The bifunctional antibody of claim 1, wherein the heavy chain variable region (VH) of the anti-PD-L1 antibody has an amino acid sequence as shown in SEQ ID NO: 1 or 8; and/or the light chain variable region (VL) of the anti-PD-L1 antibody has an amino acid sequence as shown in SEQ ID NO: 2 or 9.

11. The bifunctional antibody of claim 1, wherein the anti-VEGF element comprises a second extracellular region D2 (VEGFR1D2) of vascular endothelial growth factor receptor 1 (VEGFR1).

12. The bifunctional antibody of claim 1, wherein the bifunctional antibody has a structure shown in formula Ia or Ib from the N-terminal to the C-terminal:

$$D—L1—VH—CH; \atop VL—CL \quad (Ia)$$

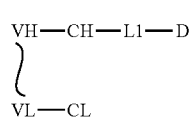

wherein,
D is the anti-VEGF element;
L1 is absent or a linker element;
VL represents the light chain variable region of the anti-PD-L1 antibody;
CL represents the light chain constant region of the anti-PD-L1 antibody;
VH represents the heavy chain variable region of the anti-PD-L1 antibody;
CH represents the heavy chain constant region of the anti-PD-L1 antibody;
"~" represents a disulfide bond;
"-" represents a peptide bond;
wherein, the bifunctional antibody has an activity of simultaneous binding PD-L1 and VEGF.

* * * * *

SEQUENCE LISTING

<160> NUMBER OF SEQ ID NOS: 16

<210> SEQ ID NO 1
<211> LENGTH: 120
<212> TYPE: PRT
<213> ORGANISM: Mus musculus

<400> SEQUENCE: 1

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Ala Phe Thr Gly Tyr
            20                  25                  30

Thr Ile His Trp Val Lys Gln Arg Ser Gly Leu Gly Leu Glu Trp Leu
        35                  40                  45

Gly Trp Phe Tyr Pro Gly Ser Gly Thr Leu Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Leu Glu Leu Ser Arg Leu Thr Ser Glu Asp Ser Ala Val Tyr Phe Cys
                85                  90                  95

Ala Arg His Gly Thr Gly Thr Leu Met Ala Met Asp Tyr Trp Gly Gln
                100                 105                 110

Gly Thr Ser Val Thr Val Ser Ser
            115                 120
```

<210> SEQ ID NO 2
<211> LENGTH: 112
<212> TYPE: PRT
<213> ORGANISM: Mus musculus

<400> SEQUENCE: 2

```
Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Pro Thr Phe Gly Gly Gly Thr Lys Leu Glu Ile Lys
            100                 105                 110

<210> SEQ ID NO 3
<211> LENGTH: 8
<212> TYPE: PRT
<213> ORGANISM: Mus musculus

<400> SEQUENCE: 3

Gly Tyr Ala Phe Thr Gly Tyr Thr
1               5

<210> SEQ ID NO 4
<211> LENGTH: 8
<212> TYPE: PRT
<213> ORGANISM: Mus musculus

<400> SEQUENCE: 4

Phe Tyr Pro Gly Ser Gly Thr Leu
1               5

<210> SEQ ID NO 5
<211> LENGTH: 13
<212> TYPE: PRT
<213> ORGANISM: Mus musculus

<400> SEQUENCE: 5

Ala Arg His Gly Thr Gly Thr Leu Met Ala Met Asp Tyr
1               5                   10

<210> SEQ ID NO 6
<211> LENGTH: 11
<212> TYPE: PRT
<213> ORGANISM: Mus musculus

<400> SEQUENCE: 6

Gln Ser Leu Ala Asn Ser Tyr Gly Asn Thr Tyr
1               5                   10

<210> SEQ ID NO 7
<211> LENGTH: 9
<212> TYPE: PRT
<213> ORGANISM: Mus musculus

<400> SEQUENCE: 7

Leu Gln Gly Thr His Gln Pro Pro Thr
1               5

<210> SEQ ID NO 8
<211> LENGTH: 120
<212> TYPE: PRT
<213> ORGANISM: Artificial Sequence
<220> FEATURE:
<223> OTHER INFORMATION: Heavy chain variable region of the anti-PD-L1
      antibody

<400> SEQUENCE: 8

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ala Phe Thr Gly Tyr
            20                  25                  30

Thr Ile His Trp Val Arg Gln Ala Pro Gly Gln Arg Leu Glu Trp Met
            35                  40                  45

Gly Trp Phe Tyr Pro Gly Ser Gly Thr Leu Lys Tyr Ser Glu Lys Phe
50                  55                  60

Gln Gly Arg Val Thr Ile Thr Arg Asp Lys Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Thr Gly Thr Leu Met Ala Met Asp Tyr Trp Gly Gln
            100                 105                 110

Gly Thr Leu Val Thr Val Ser Ser
            115                 120

<210> SEQ ID NO 9
<211> LENGTH: 112
<212> TYPE: PRT
<213> ORGANISM: Artificial Sequence
<220> FEATURE:
<223> OTHER INFORMATION: Light chain variable region of the anti-PD-L1
      antibody

<400> SEQUENCE: 9

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Ala Asn Ser
            20                  25                  30

Tyr Gly Asn Thr Tyr Leu Ser Trp Tyr Leu His Lys Pro Gly Gln Ser
            35                  40                  45

Pro Gln Leu Leu Ile Tyr Gly Ile Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Pro Thr Phe Gly Gln Gly Thr Lys Leu Glu Ile Lys
            100                 105                 110

<210> SEQ ID NO 10
<211> LENGTH: 100
<212> TYPE: PRT
<213> ORGANISM: Artificial Sequence
<220> FEATURE:
<223> OTHER INFORMATION: Second extracellular region of vascular
      endothelial growth factor 1

<400> SEQUENCE: 10

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80
```

```
Ala Thr Val Asn Gly His Leu Tyr Lys Thr Asn Tyr Leu Thr His Arg
                85                  90                  95

Gln Thr Asn Thr
            100

<210> SEQ ID NO 11
<211> LENGTH: 564
<212> TYPE: PRT
<213> ORGANISM: Artificial Sequence
<220> FEATURE:
<223> OTHER INFORMATION: Heavy chain of the bifunctional antibody

<400> SEQUENCE: 11

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Gly Gly Ser Gly Gly Ser Gly Gly Ser Gly Gly Ser
            100                 105                 110

Gly Gly Ser Gln Val Gln Leu Val Gln Ser Gly Ala Glu Val Lys Lys
        115                 120                 125

Pro Gly Ala Ser Val Lys Val Ser Cys Lys Ala Ser Gly Tyr Ala Phe
    130                 135                 140

Thr Gly Tyr Thr Ile His Trp Val Arg Gln Ala Pro Gly Gln Arg Leu
145                 150                 155                 160

Glu Trp Met Gly Trp Phe Tyr Pro Gly Ser Gly Thr Leu Lys Tyr Ser
                165                 170                 175

Glu Lys Phe Gln Gly Arg Val Thr Ile Thr Arg Asp Lys Ser Leu Ser
            180                 185                 190

Thr Ala Tyr Met Glu Leu Ser Ser Leu Arg Ser Glu Asp Thr Ala Val
        195                 200                 205

Tyr Tyr Cys Ala Arg His Gly Thr Gly Thr Leu Met Ala Met Asp Tyr
    210                 215                 220

Trp Gly Gln Gly Thr Leu Val Thr Val Ser Ser Ala Ser Thr Lys Gly
225                 230                 235                 240

Pro Ser Val Phe Pro Leu Ala Pro Ser Ser Lys Ser Thr Ser Gly Gly
                245                 250                 255

Thr Ala Ala Leu Gly Cys Leu Val Lys Asp Tyr Phe Pro Glu Pro Val
            260                 265                 270

Thr Val Ser Trp Asn Ser Gly Ala Leu Thr Ser Gly Val His Thr Phe
        275                 280                 285

Pro Ala Val Leu Gln Ser Ser Gly Leu Tyr Ser Leu Ser Ser Val Val
    290                 295                 300

Thr Val Pro Ser Ser Ser Leu Gly Thr Gln Thr Tyr Ile Cys Asn Val
305                 310                 315                 320

Asn His Lys Pro Ser Asn Thr Lys Val Asp Lys Arg Val Glu Pro Lys
                325                 330                 335
```

-continued

```
Ser Cys Asp Lys Thr His Thr Cys Pro Pro Cys Pro Ala Pro Glu Ala
                340                 345                 350

Ala Gly Gly Pro Ser Val Phe Leu Phe Pro Pro Lys Pro Lys Asp Thr
            355                 360                 365

Leu Met Ile Ser Arg Thr Pro Glu Val Thr Cys Val Val Val Asp Val
    370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Glu Glu Met Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly

<210> SEQ ID NO 12
<211> LENGTH: 564
<212> TYPE: PRT
<213> ORGANISM: Artificial Sequence
<220> FEATURE:
<223> OTHER INFORMATION: Heavy chain of the bifunctional antibody

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Gly Tyr
            20                  25                  30

Thr Ile His Trp Val Arg Gln Ala Pro Gly Gln Arg Leu Glu Trp Met
        35                  40                  45

Gly Trp Phe Tyr Pro Gly Ser Gly Thr Leu Lys Tyr Ser Glu Lys Phe
    50                  55                  60

Gln Gly Arg Val Thr Ile Thr Arg Asp Lys Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Thr Gly Thr Leu Met Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Ser Gly Gly Ser Gly Gly Ser Gly Gly Ser Gly Gly Ser
    450                 455                 460

Ser Asp Thr Gly Arg Pro Phe Val Glu Met Tyr Ser Glu Ile Pro Glu
465                 470                 475                 480

Ile Ile His Met Thr Glu Gly Arg Glu Leu Val Ile Pro Cys Arg Val
                485                 490                 495

Thr Ser Pro Asn Ile Thr Val Thr Leu Lys Lys Phe Pro Leu Asp Thr
            500                 505                 510

Leu Ile Pro Asp Gly Lys Arg Ile Ile Trp Asp Ser Arg Lys Gly Phe
        515                 520                 525

Ile Ile Ser Asn Ala Thr Tyr Lys Glu Ile Gly Leu Leu Thr Cys Glu
    530                 535                 540
```

```
Ala Thr Val Asn Gly His Leu Tyr Lys Thr Asn Tyr Leu Thr His Arg
545                 550                 555                 560

Gln Thr Asn Thr

<210> SEQ ID NO 13
<211> LENGTH: 219
<212> TYPE: PRT
<213> ORGANISM: Artificial Sequence
<220> FEATURE:
<223> OTHER INFORMATION: Light chain of the bifunctional antibody

<400> SEQUENCE: 13

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 5
<212> TYPE: PRT
<213> ORGANISM: Artificial Sequence
<220> FEATURE:
<223> OTHER INFORMATION: Linker Peptide

<400> SEQUENCE: 14

Gly Gly Gly Gly Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Linker Peptide
```

```
<400> SEQUENCE: 15

Gly Gly Gly Gly Ser Gly Gly Gly Ser
1               5

<210> SEQ ID NO 16
<211> LENGTH: 15
<212> TYPE: PRT
<213> ORGANISM: Artificial Sequence
<220> FEATURE:
<223> OTHER INFORMATION: Linker Peptide

<400> SEQUENCE: 16

Gly Gly Ser Gly Gly Ser Gly Gly Ser Gly Gly Ser Gly Gly Ser
1               5                   10                  15
```